United States Patent [19]
Jonas et al.

[11] Patent Number: 4,731,449
[45] Date of Patent: Mar. 15, 1988

[54] MELTABLE, ELECTRICALLY CONDUCTING TCNQ COMPLEXES

[75] Inventors: Friedrich Jonas, Aachen; Jürgen Hocker, Bergisch-Gladbach, both of Fed. Rep. of Germany

[73] Assignee: Bayer Aktiengesellschaft, Leverkusen, Fed. Rep. of Germany

[21] Appl. No.: 835,337

[22] Filed: Mar. 3, 1986

[30] Foreign Application Priority Data

Mar. 14, 1985 [DE] Fed. Rep. of Germany ....... 3509070

[51] Int. Cl.$^4$ ................. C07D 211/78; C07D 211/90; C07D 213/79; C07D 211/70
[52] U.S. Cl. .................................... 546/286; 546/318; 546/326; 546/314; 546/315; 546/330; 260/396 N
[58] Field of Search ............... 546/286, 318, 326, 314, 546/315, 330; 260/396 N

[56] References Cited

U.S. PATENT DOCUMENTS 3,162,641 12/1964 Acker et al. ......................... 546/286
3,947,792 3/1976 Reuting ............................... 546/286

FOREIGN PATENT DOCUMENTS 2329492 1/1974 Fed. Rep. of Germany ...... 546/286

OTHER PUBLICATIONS

The Journal of the American Chemical Society, Author: Melby et al, Titled: Substituted Quinodimethans, II. Anion-Radical Derivatives and Complexes of 7,7,8,8-tetracyanoquinodimethan, Dated: Mar. 15, 1962; vol. 84, pp. 3374–3387.

*Primary Examiner*—Henry R. Jiles
*Assistant Examiner*—Robert C. Whittenbaugh
*Attorney, Agent, or Firm*—Connolly & Hutz

[57] ABSTRACT

TCNQ complexes with organic pyridinium ions, which may be kept in a molten condition for a relatively long time without the electrical conductivity thereof being substantially reduced after cooling.

2 Claims, No Drawings

MELTABLE, ELECTRICALLY CONDUCTING TCNQ COMPLEXES

Complex salts of the 7,7,8,8-tetracyano-p-quinodimethane anion (TCNQ)$^\ominus$, $$\left[ \begin{array}{c} NC \\ NC \end{array} \!\!=\!\! \underset{}{\bigcirc} \!\!=\!\! \begin{array}{c} CN \\ CN \end{array} \right]^{-}$$

neutral, 7,7,8,8-tetracyano-p-quinodimethane (TCNQ) and inorganic or organic cations are known as electrically conducting compounds and may be produced by reacting TCNQ with organic cation iodides [J. Am. Chem. Soc. 84, 3374–3378 (1962)], for example:

Reaction Scheme I $$4\ TCNQ + 3M^+I^- \longrightarrow 2\ (M^+.TCNQ^-.TCNQ) + M^+I_3^-$$

wherein M is e.g. an N-alkyl quinolinium cation. One TCNQ molecule is reduced by iodide to the TCNQ radical anion with the release of iodine.

Another process involves reacting nitrogen-containing heteroaromatics or tertiary amines with H$_2$TCNQ and TCNQ, for example:

Reaction Scheme II $$3\ TCNQ + \underset{H_2TCNQ}{\begin{array}{c} NC \\ NC \end{array}\!\!HC\!\!-\!\!\bigcirc\!\!-\!\!CH\!\!\begin{array}{c} CN \\ CN \end{array}} +$$

$$2(C_2H_5)_3N \longrightarrow 2(C_2H_5)_3NH.(TCNQ)_2^-$$

The processing of these complexes at temperatures above the melting point thereof presents problems, since the known compounds decompose at the melting point or slightly above the melting point (see Table 1).

It has been found that complexes of TCNQ and certain organic pyridinium ions may be kept in a molten state for a relatively long time without the electrical conductivity thereof being substantially reduced after cooling.

The present invention thus provides TCNQ complexes corresponding to the following general formula (I):

$$\left[ \underset{R^5}{\overset{R^4}{\bigotimes}}\!\!\underset{R^{1\oplus}}{\overset{R^3\ X}{\underset{N}{\bigotimes}}}\!\!-\!\!R^2 \right]^{\oplus} \left[ \begin{array}{c} NC \\ NC \end{array}\!\!=\!\!\bigcirc\!\!=\!\!\begin{array}{c} CN \\ CN \end{array} \right]^{\ominus} \left[ \begin{array}{c} NC \\ NC \end{array}\!\!=\!\!\bigcirc\!\!=\!\!\begin{array}{c} CN \\ CN \end{array} \right]_n \tag{I}$$

wherein $2 \geq n \geq 0$, preferably $1 \geq n \geq 0$;

$R^1$, $R^2$, $R^3$, $R^4$, $R^5$, which may be the same or different, represent hydrogen or an optionally substituted straight- or branched-chain alkyl radical having from 1 to 30 carbon atoms, an optionally substituted cycloalkyl radical having from 5 to 12 carbon atoms, an optionally substituted aryl radical having from 6 to 14 carbon atoms or a heterocyclic radical having from 4 to 12 carbon atoms, with the proviso that $R^1 \neq$ hydrogen; and X represents one of the following groups:

$$-CN, \ -\overset{O}{\underset{\|}{C}}-OR, \ -\overset{O}{\underset{\|}{C}}-R$$

wherein R is defined as for $R^1$. The following formulae are given as examples for $R^1$ and R:

CH$_3$—CH$_2$—CH$_2$—   CH$_3$—CH$_2$—CH$_2$—CH$_2$—

$$CH_3-CH_2-\underset{CH_3}{\overset{}{CH}}- \qquad \underset{CH_3}{\overset{CH_3}{\diagdown}}CH-$$

CH$_3$—CH$_2$—CH$_2$—CH$_2$—CH$_2$—
CH$_3$—CH$_2$—CH$_2$—CH$_2$—CH$_2$—CH$_2$—
CH$_3$—CH$_2$—CH$_2$—CH$_2$—CH$_2$—CH$_2$—CH$_2$—
CH$_3$—CH$_2$—CH$_2$—CH$_2$—CH$_2$—CH$_2$—CH$_2$—CH$_2$—CH$_2$—

CH$_3$—CH$_2$   CH$_3$—CH$_2$—CH$_2$—CH$_2$—$\underset{C_2H_5}{\overset{}{CH}}$—CH$_2$—
CH$_3$—

CH$_2$=CH—CH$_2$—

$$\underset{H}{\bigcirc}- \quad \underset{H}{\bigcirc}- \quad \underset{H}{\bigcirc}-$$

Particularly preferred are compounds (I) wherein $R^2$, $R^3$, $R^4$ and $R^5$ represent hydrogen and $R^1$, R independently represent C$_1$–C$_{12}$ alkyl.

Most preferred are TCNQ complex salts corresponding to formula (II):

$$A^\oplus (TCNQ)^\ominus (TCNQ)_n$$

wherein $2 \geq n \geq 0$; and $A^\oplus$ represents a cation corresponding to one of the following formulae $$\underset{\underset{R}{\overset{|}{N_\oplus}}}{\bigcirc}\!\!-\!\!CN \ ; \quad \underset{\underset{R}{\overset{|}{N_\oplus}}}{\bigcirc}\!\!-\!\!\overset{O}{\underset{\|}{C}}\!\!-\!\!OR^1 \ ; \quad \underset{\underset{R}{\overset{|}{N_\oplus}}}{\bigcirc}\!\!-\!\!\overset{O}{\underset{\|}{C}}\!\!OR^1 \ ;$$

IIIa      IIIb      IIIc

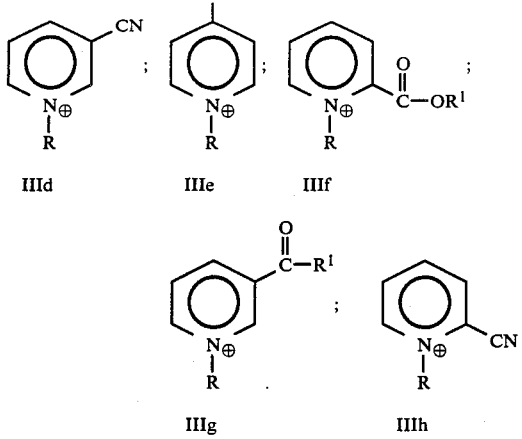

IIId    IIIe    IIIf

IIIg    IIIh wherein R and R¹, which may be the same or different, represent an optionally substituted straight- or branched-chain alkyl radical having from 1 to 30 carbon atoms, an optionally substituted cycloalkyl radical having from 5 to 12 carbon atoms, an optionally substituted aryl radical having from 6 to 14 carbon atoms or a heterocyclic radical having from 4 to 12 carbon atoms.

The complexes (I) may be produced according to reaction scheme (I) as described in J. Am. Chem. Soc. 84, 3374–3387 (1962).

The production of the compounds according to the present invention advantageously takes place by reacting solutions of substituted, organic pyridinium iodides with a solution of TCNQ in organic solvents at temperatures below 150° C.

Suitable organic solvents are, for example, halogenated hydrocarbons, for example methylene chloride, chloroform, carbon tetrachloride, 1,2-dichloroethane, 1,1,2-trichloroethane; acetonitrile; alcohols, for example methanol, ethanol, isopropanol; aliphatic ketons, for example acetone, methylethyl ketone; acrylic and cyclic ethers, for example diethyl ether, tetrahydrofuran.

The reactants are generally used in a ratio of 1 mol of TCNQ to from 0.5 to 1.5 mol of pyridinium iodide.

Owing to the favourable melting and decomposition behaviour thereof, the compounds (I) may be used for the production of electrically-conducting coatings on substrates by melt-coating.

Mixtures of different TCNQ complexes which contain at least one compound (I) may also be processed from the melt in advantageous manner to form conducting coatings. Such coatings may optionally also contain stabilisers or colouring additives or shore which improve adhesion or lower the melting point.

The following are mentioned as suitable substrates: glass, metals, metal oxides, organic polymers.

The coating of the substrates may take place in such a manner that the substrates are heated to temperatures above the melting point of the TCNQ complexes (I) and the solid TCNQ complexes are then applied to the substrate surface.

Melt-coating of the TCNQ complexes is possible also under protective gasses, such as hydrogen, nitrogen, argon or helium, or under vacuum.

In another process, the procedure is such that the TCNQ complexes (I) are applied to the substrates to be coated at room temperature and are then melted on in a preheated furnace.

The possibility also exists of coating substrates by immersing them in a melt of the complexes (I).

These processes result in electrically conducting coatings having good adhesion.

Coatings produced in this manner are used in the electronics industry.

EXAMPLE 1

20.4 g of TCNQ in 1000 ml of acetonitrile are refluxed with a 70° C. hot solution of 22.0 g of 1-methyl-4-carbethoxy-pyridinium iodide in 100 ml of acetonitrile and stirred for 10 minutes. Cooling is then carried out and the precipitate crystallized to completion overnight is separated by suction and dried. With complexes having good solubility, the yield may be increased by concentrating the mother liquor.

Yield: 24.4 g (85% of the theoretical value)
Complex of the composition:

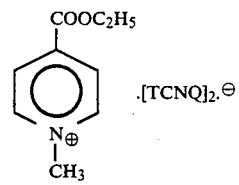

EXAMPLE 2

As described in Example 1, 10.2 g of TCNQ in 500 ml of acetonitrile and 11 g of 1-methyl-2-carbethoxy-pyridinium iodide in 100 ml of acetonitrile are reacted and worked up.

Yield: 12.6 g (88% of the theoretical value)
Complex of the composition:

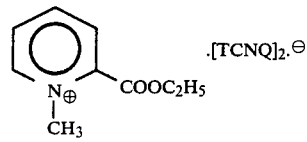

EXAMPLE 3

As described in Example 1, 10.2 g of TCNQ in 400 ml of acetonitrile and 9.9 g of 1-methyl-4-acetyl-pyridium iodide in 100 ml of acetonitrile are reacted and worked-up.

Yield: 11.7 g (86% of the theoretical value)
Complex of the composition:

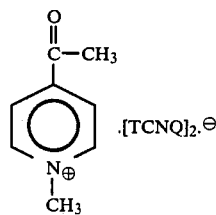

EXAMPLE 4

As described in Example 1, 10.2 g of TCNQ in 400 ml of acetonitrile and 9.8 g of 1-ethyl-4-cyano-pyridinium iodide in 100 ml of acetonitrile are reacted and worked-up.

Yield: 12.0 g (89% of the theoretical value)
Complex of the composition:

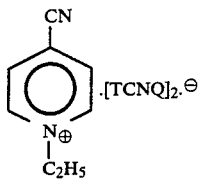

The thermal stability of the complexes according to Examples 1 to 4 may be seen from Table 1. The complexes were melted in glass containers at 260° C. for 30 sec and cooled to room temperature. The conductivity of the pure complexes $\delta^o$ before melting or of the solidified melts $\delta^s$ were determined by means of four-electrode measurement under pressure (250 kp/cm²).

TABLE 1

| complex according to Example | $\delta^o$ S/cm | $\delta^s$ S/cm |
|---|---|---|
| 1 | 1.6 | 0.25 |
| 2 | 0.5 | 0.2 |
| 3 | 0.8 | 0.06 |
| 4 | 0.08 | 0.01 |
| comparison | 0.5 | $5 \cdot 10^{-8}$ | comparison:

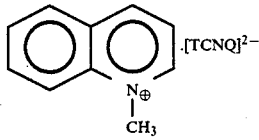

EXAMPLES 5-8

About 0.5 mm thick layers of the complexes 1-5 were scattered onto glass plates and then heated in a hot air furnace at an air temperature of 300° C., until a homogeneous melt was produced.

In all cases, hard, glossy electrically conductive coatings were obtained.

We claim:

1. TCNQ complex salts corresponding to the following general formula (I):

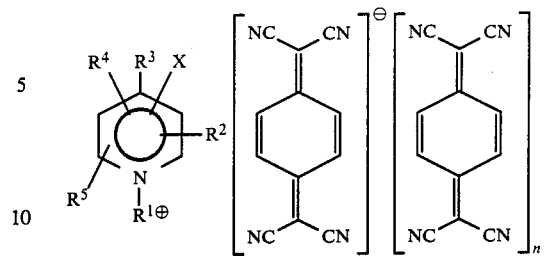

wherein
$2 \geq n \geq 0$;
$R^1$, $R^2$, $R^3$, $R^4$, $R^5$, which may be the same or different, represent hydrogen, a straight- or branched-chain alkyl radical having from 1 to 30 carbon atoms or a cycloalkyl radical having from 5 to 12 carbon atoms with the proviso that $R^1$ is not hydrogen; and X represents

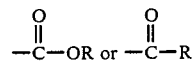

wherein R is defined as for $R^1$.

2. TCNQ complex salts corresponding to formula (II):

$$A^{\oplus}(TCNQ)^{\ominus}(TCNQ)_n \qquad (II)$$

wherein
$2 \geq n \geq 0$; and
$A^{\oplus}$ represents a cation corresponding to one of the following formulae

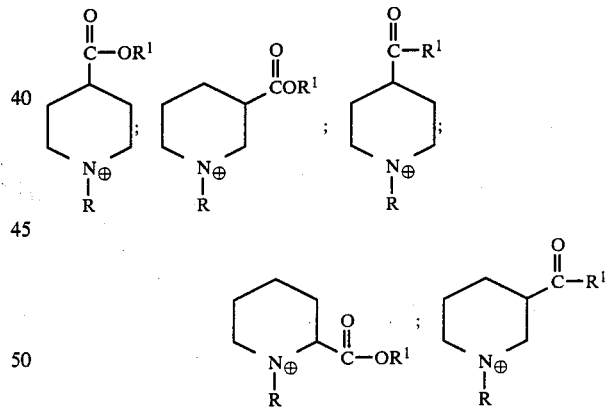

wherein R and $R^1$, which may be the same or different, represent a straight- or branched-chain alkyl radical having from 1 to 30 carbon atoms or a cycloalkyl radical having from 5 to 12 carbon atoms.

* * * * *

UNITED STATES PATENT AND TRADEMARK OFFICE
CERTIFICATE OF CORRECTION

PATENT NO. : 4,731,449

DATED : March 15, 1988

INVENTOR(S) : JONAS ET AL

It is certified that error appears in the above-identified patent and that said Letters Patent is hereby corrected as shown below:

The formulae beginning at column 6, lines 36-53 should be depicted,

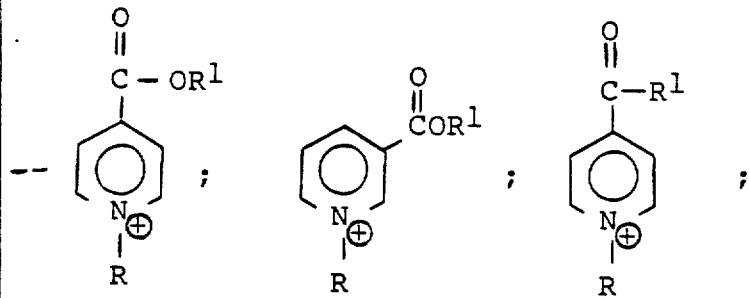

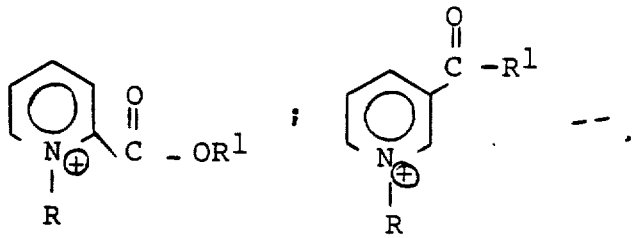

--.

Signed and Sealed this

Fourth Day of October, 1988

*Attest:*

DONALD J. QUIGG

*Attesting Officer*   Commissioner of Patents and Trademarks